US006465248B1

(12) United States Patent
Commissiong

(10) Patent No.: US 6,465,248 B1
(45) Date of Patent: Oct. 15, 2002

(54) METHODS FOR PRODUCING AND PREPARING CELLS FOR CELL THERAPY

(75) Inventor: John Commissiong, Mississauga (CA)

(73) Assignee: Prescient NeuroPharma, Inc., Toronto (CA)

( * ) Notice: Subject to any disclaimer, the term of this patent is extended or adjusted under 35 U.S.C. 154(b) by 0 days.

(21) Appl. No.: 09/616,505

(22) Filed: Jul. 14, 2000

Related U.S. Application Data

(60) Provisional application No. 60/144,360, filed on Jul. 16, 1999.
(51) Int. Cl.[7] .............................. C12N 5/08; C12N 5/00; C12N 5/10; C12N 5/02
(52) U.S. Cl. ........................ 435/368; 435/383; 435/384; 435/377; 435/363; 435/325
(58) Field of Search .................................. 435/325, 383, 435/363, 368, 377, 384

(56) References Cited

U.S. PATENT DOCUMENTS

| | | | |
|---|---|---|---|
| 5,411,883 A | 5/1995 | Boss et al. ................... | 435/240 |
| 5,750,376 A | 5/1998 | Weiss et al. .............. | 435/69.52 |

FOREIGN PATENT DOCUMENTS

| | | |
|---|---|---|
| WO | WO 99/21966 | 5/1999 |

OTHER PUBLICATIONS

Spector et al. "A Model Three–dimensional Culture System for Mammalian Dopaminergic Precursor Cells: Application for Functional Intracerebral Transplantation," *Experimental Neurology* 124:253–264 (1993).

Espejo et al., "Intrastriatal grafts of fetal mesencephalic cell suspensions in MPP+–lesioned rats: a microdialysis study in vivo," *Neurochemical Research* 23:1217–1223 (1998).

Espejo et al., "Cellular and functional recovery of parkinsonian rats after intrastriatal transplantation of carotid body cell aggregates," *Neuron* 20:197–206 (1998).

Flax et al., "Engraftable human neural stem cells respond to developmental cues, replace neurons, and express foreign genes," *Nature Biotechnology* 16:1033–1039 (1998).

Shimoda et al., "A high percentage yield of tyrosine hydroxylase–positive cells from rat E14 mesencephalic cell culture," *Brain Res.* 586:319–331 (1992).

(List continued on next page.)

*Primary Examiner*—James Ketter
*Assistant Examiner*—Q. Janice Li
(74) *Attorney, Agent, or Firm*—Kristina Bieker-Brady; Clark & Elbing LLP

(57) ABSTRACT

The invention features methods for expansion and packaging of cells. Expansion is achieved by providing cells that include neural progenitor cells; plating the cells in culture vessels at an average density of $1 \times 10_5$ to $7 \times 10_5$ cells/cm$^2$; and culturing said cells in culture medium and under conditions permissible for proliferation of said neural progenitor cells, wherein the volume of medium results in an initial cell density of between $5 \times 10_4$ and $1.5 \times 10_5$ cells per milliliter of medium. Preparation of cells for transplantation includes providing a cell suspension that includes single cells, aggregates of fewer than two hundred cells, or a combination thereof; and re-aggregating the cells in said cell suspension, wherein greater than 50% of reaggregates consist of between 25 and 500 cells/reaggregate.

10 Claims, 5 Drawing Sheets

OTHER PUBLICATIONS

Studer et al., "Transplantation of expanded mesencephalic precursors leads to recovery in parkinsonian rats," *Nature Neuroscience* 1:290–295 (1998).

Takeshima et al., "Mesencephalic type 1 astrocytes rescue dopaminergic neurons from death induced by serum deprivation," *J. Neurosci.* 14:4769–4779 (1994).

Takeshima et al., "Astrocyte–dependent and –independent phases of the development and survival of rat embryonic day 14 mesencephalic, dopaminergic neurons in culture," *Neuroscience* 60:809–823 (1994).

Takeshima et al., "Standardized methods to bioassay neurotrophic factors for dopaminergic neurons," *J. Neurosci. Methods* 67:27–41 (1996).

Takeshima et al., "Robust expansion of rate E12 mesencephalic dopaminergic neurons in culture," *Soc. Neurosci. Abstr.* 23: 593 (Abstr. 239.10) (1997).

Wagner et al., "Induction of a midbrain dopaminergic phenotype in Nurr 1–overexpressing neural stem cells by type 1 astrocytes," *Nature Biotechnology* 17:653–659 (1999).

Commissiong et al., "Effects of Transforming Growth Factors on Dopaminergic Neurons in Culture," Neurochem, Int. 30:393–399 (1997).

Gage, "Discussion Point: Stem Cells of the Central Nervous System," Current Opinion in Neurobiolgy 8:671–676 (1998).

Panchision et al., "An Immortalized, Type–1 Astrocyte of Mesencephalic Origin Source of a Dopaminergic Neurotrophic Factor," Journal of Molecular Neuroscience 11:209–221 (1998).

Studer et al., "Transplantation of Expanded Mescencephalic Precursors Leads to Recovery in Parkinsonian Rats," Nature Neuroscience 1:290–295 (1998).

METHODS FOR PRODUCING AND PREPARING CELLS FOR CELL THERAPY

CROSS-REFERENCE TO RELATED APPLICATIONS

This application claims priority from U.S. Provisional Application No. 60/144,360, filed Jul. 16, 1999 (now pending), which is hereby incorporated by reference.

BACKGROUND OF THE INVENTION

The invention relates to methods of producing and packaging cells for cell therapy treatment of neurological disorders.

A large number of human neurological disorders result from the death of neural cells. One strategy for treating a person having such a disorder is to transplant cells (e.g., neurons, glia, precursor cells, progenitor cells, or stem cells) into the patient's brain. For example, dopamine-secreting cells derived from fetal brain have been used successfully to correct motor deficits induced by acute lesions of the dopaminergic nigrostriatal pathway in rat and monkey animal models for Parkinson's disease.

A major impediment in the use of cell therapy treatment for the treatment of neurological disorders such as, for example, Parkinson's disease, stroke, and multiple sclerosis is the lack of an adequate supply of the appropriate cells. In Parkinson's disease, fetal pig dopaminergic neurons have been tested as a possible solution to the problem posed by the shortage of human cells (Deacon et al., Nature Med. 3:350–353, 1997). Apart from the immunologic problems posed by xenografting, the demonstrated transfer of pig viruses to human cells will likely impede the development of this line of investigation.

Even with the presence of sufficient numbers of cells for transplantation, there is a second fundamental problem that needs to be addressed: the cells, whether they be human or otherwise, and whether they be neurons, precursor cells, or stem cells, need to be properly prepared for transplantation into the brain of the recipient. In the past, approximately 95% of the transplanted cells have failed to survive (Kordower et al., Mov. Disord. 13: 88–95 (Suppl.), 1998). Compounding the problem, current methods of preparing cells for transplantation often reduce cell viability prior to transplantation.

In order to improve cell therapy for the treatment of a patient having a neurological disorder, one must overcome the lack of an adequate supply of cells and improve the viability of the cells prior to and during transplantation. Thus, there is a need for improved culture methods for the production of cells for transplantation, and for improved cell packaging methods for maintaining cell viability during before and during the transplantation procedure.

SUMMARY OF THE INVENTION

We have discovered a highly feasible solution to the shortage of cells for cell transplantation therapy by the way of improved in vitro expansion of cells that are the progenitors of neurons and glia. These progenitor cells can be made to differentiate in vitro prior to transplantation, or they can be transplanted as progenitors and allowed to differentiate in vivo. In either case, we prove herewith, novel steps which may be utilized to ensure the viability of these or any other cells following transplantation.

To achieve this goal, we have developed a culture system which results in the expansion in the number of progenitor cells and an increase in the number of dopaminergic neurons. This system can be readily adapted to large scale culture, allowing for the in vitro production of neurons for the treatment of diseases such as Parkinson's disease.

The culture system of the present invention further results in increased cell viability before and during transplantation. Thus, not only are more cells available for transplantation, but a greater percentage are viable immediately before and following the transplantation. In human cell therapy protocols, this is highly likely to result in greater behavioral improvement in the treated patient.

Accordingly, in a first aspect, the invention features a method for expansion of neural progenitor cells in vitro. The method includes: (a) providing cells that include neural progenitor cells; (b) plating the cells in culture vessels at an average density of $1 \times 10^5$ to $7 \times 10^5$ cells/cm$^2$; and (c) culturing the cells in culture medium and under conditions permissible for proliferation of the neural progenitor cells, wherein the volume of medium results in an initial density of between $5 \times 10^4$ and $1.5 \times 10^5$ cells per milliliter of medium.

In one preferred embodiment, prior to the plating of the cells, the culture vessels are coated with polyornithine, fibronectin, or a combination thereof.

Preferably, the culture medium includes fibroblast growth factor. In a preferred embodiment, the concentration is between 2 ng and 100 ng per milliliter and, even more preferably, is between 2 ng and 15 ng per milliliter. The culture medium can also include insulin.

The neural progenitor cells can be any neural progenitor cells (e.g., multipotent progenitor cells, precursor cells, or multipotent stem cells) that can differentiate as neurons, glia, or both. The neural progenitor cells can also include cells that contain a transgene. Preferably, the neural progenitors are progenitors of dopaminergic neurons, and are capable of expressing tyrosine hydroxylase and secreting dopamine. In a preferred embodiment, the neural progenitor cells are from a human.

Preferably, the cells are plated as microislands. The microislands, at the time of plating, are, on average, between 2,000 and 25,000 cells per microisland, more preferably, are between 2,000 and 6,000 cells per microisland, and, most preferably, are between 3,000 and 5,000 cells per microisland.

In a second aspect, the invention features a method for preparing cells for transplantation. The method includes: (a) providing a cell suspension that includes single cells, aggregates of fewer than 500 cells, or a combination thereof; and (b) re-aggregating cells so that greater than 50% of reaggregates have between 25 and 500 cells. Preferably, 75% or more of the reaggregates have between 25 and 500 cells and, most preferably, 90% or more of the reaggregates have between 25 and 500 cells. In particularly preferred embodiments, 90% or more of the reaggregates have between 50 and 200 cells or even between 75 and 150 cells.

In one preferred embodiment, the cells in the reaggregate include cells expressing tyrosine hydroxylase. Preferably, at least 20%, 30% or even 50% of the cells are tyrosine hydroxylase-positive. More preferably, the tyrosine hydroxylase-positive cells secrete dopamine. The cells, preferably, are human cells.

In a third aspect, the invention features a cell aggregate for use in transplantation therapy, the aggregate including 25 to 500 cells. Preferably, greater than 20%, 30%, or even 50% of the cells are tyrosine hydroxylase-positive. It is highly desirable that the tyrosine-hydroxylase cells secrete dopamine. In preferred embodiments, the cell aggregate of the third aspect contains 50 to 200 cells or even 75 to 150 cells. While the cells can be from any animal, it is preferred that the aggregates contain human cells.

The present invention provides improved methods for expanding progenitor cell populations, inducing terminal differentiation, and packaging the cells for transplantation.

Other features and advantages of the invention will be apparent from the following description of the preferred embodiments thereof and from the claims.

DETAILED DESCRIPTION OF THE INVENTION

Figure 1A:
FIGS. 1A and 1B are a series of photographs of tyrosine hydroxylase-positive (TH-positive)(FIG. 1A) and MAP2-positive (FIG. 1B) neurons expanded in vitro for nine days from tissue dissected from the medial ventral mesencephalon of the E12 rat brain, using bFGF (10 ng/ml) as the mitogen, followed by maturation for three days following withdrawal of the mitogen.
Figure 1B:
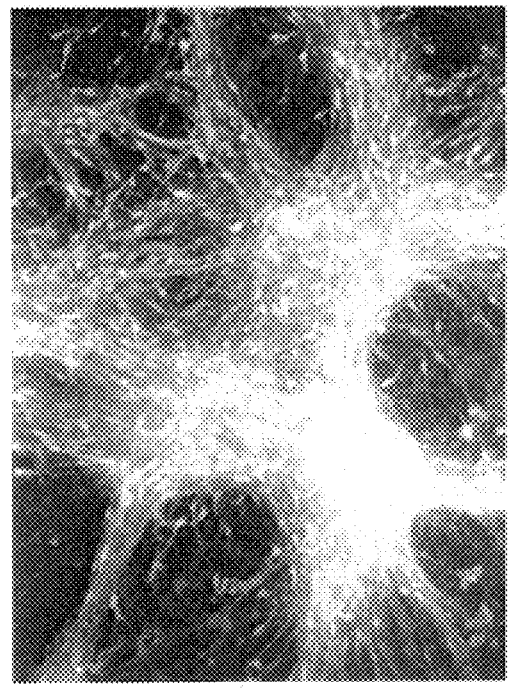
Figure 2A:
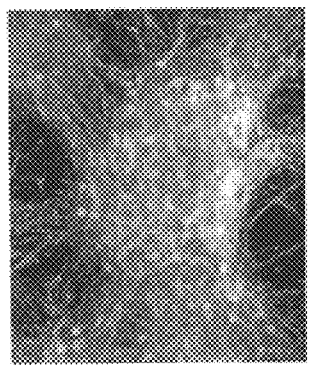
FIGS. 2A–2D are a series of photographs showing clusters of TH-positive (FIGS. 2A and 2D) and MAP2-positive (FIGS. 2B and 2C) neurons expanded in vitro for nine days from tissue dissected from rat E12, ventral mesencephalic tissue, followed by maturation for three days following withdrawal of the mitogen. Scale Bar: 50 µm.
Figure 2B:
Figure 2C:
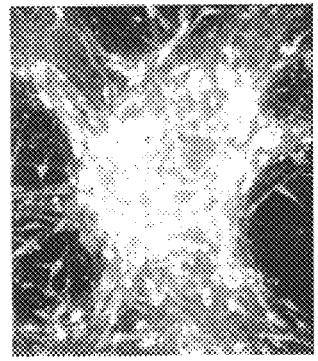
Figure 2D:
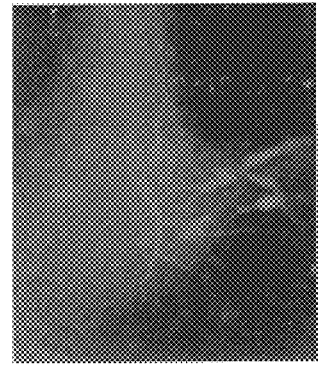

We have developed a method for large-scale production of dopaminergic neurons in vitro, in which 5-fold the normal number of primary, differentiated dopaminergic neurons per ventral mesencephalon were produced. The expanded cells were detached and reformed into small aggregates of 50 to 200 cells, that will likely yield optimal functional benefit after transplantation. The cell aggregates remained at 95% viability for six hours, in DPBS (0 mM $Ca^{2+}$, 0 mM $Mg^{2+}$) at 4° C. Cell death increased rapidly at the center of the aggregate as a function of aggregate size, indicating that cells at the center of minced fetal neural tissue normally used in clinical transplantation may not be viable.

Preparation of Cells for Transplantation

Using the methods described herein, one can prepare cells for transplantation as part of a cell therapy approach for the treatment of a neurological disorder, such as one resulting from trauma (e.g., stroke, ischemia, hypoxia) or neurodegeneration (e.g., Alzheimer's disease, Parkinson's disease, multiple sclerosis). Cell aggregates are delivered to the desired CNS or peripheral nervous system (PNS) regions using standard techniques known in the art.

Broad Applicability of Aggregation Method

Those in the art will recognize that aggregation technique that resulted in increased dopaminergic cell viability can readily be transferred to other cell types. Thus, any aggregation of neurons, glia, stem cells, progenitor cells, precursor cells, or combination thereof will have greater cell viability when aggregated using the present method.

Aggregates of 25–500 cells is preferred over smaller aggregates (i.e., fewer than 25 cells per aggregate. In neurons, larger aggregates allows for the maintenance of axonal and dendritic processes, which otherwise will be sheared off during the dispersion of the cells. The presence of the processes results in more rapid integration of the grafted cells into the host tissue. We have discovered that if cell aggregates are too large (e.g., greater than 500 cells per aggregate), then there is a loss of cell viability at the center of the aggregates. Thus, the desirable number of cells per aggregate should be between 25 and 500, and preferably between 50 and 200 or even between 75 and 150. It is understood that aggregation methods are not likely to produce cell aggregates of uniform size. Even if some of the aggregates are greater than 500 cells or fewer than 25 cells, the collection of aggregates will still provide the advantages described herein. Preferably, greater than 50% of the aggregates are between 25 and 500 cells, more preferably greater than 75%, and most preferably greater than 90%. The optimal collection of aggregates is one in which greater than 90% of the aggregates have between 50 and 200 cells or even between 75 and 150 cells.

Cell Therapy for the Treatment of Parkinson's Disease

In one embodiment, the method of the present invention is used to increase the production of dopaminergic neurons. These neurons can be used for the treatment of Parkinson's disease, a disease in which the central feature is loss of dopaminergic midbrain neurons.

Expression vectors, encoding an anti-apoptotic protein or other therapeutic protein, such as a growth or trophic factor (e.g., GDNF, neurturin, BDNF, bFGF, NT-3, TGF-β), a transcription factor (e.g., Nurr-1), or an immunosuppressant and operably linked to a suitable promoter, may also be introduced into cells ex vivo in order to enhance the survival of cell transplants or increase the percentage of cells that adopt the desired cell type. For example, the vectors may be introduced into progenitor cells that are capable of differentiating as dopaminergic neurons prior to transplantation into Parkinson's patients. Transplanted cells containing the expression vectors of the invention are more likely to survive in the patient after transplantation than cells not containing such vectors.

The following examples are to illustrate the invention. They are not meant to limit the invention in any way.

EXAMPLE 1

Expansion of Cells that are Progenitors of Dopaminergic Neurons

E12 rat mesencephalic cells were dissected, dissociated, and plated in culture as microislands (MI). Approximately 75% of the plated cells died by three days in vitro (DIV3). Thereafter, small clusters of cells within each MI became evident, and expanded rapidly. The mitogen, basic fibroblast growth factor, was withdrawn on DIV9, and the cells were allowed to differentiate and mature until DIV12. The cells were then double-stained for the neuron-specific marker microtubule-associated protein 2 (MAP2), and tyrosine hydroxylase (TH) (FIG. 1A). In these experiments, greater than 50% of the neurons produced by the expanded neural progenitors are TH-positive. We determined that the number of TH-positive neurons produced using this method was increased five-fold over the number of TH-positive neurons found in the rat mesencephalon.

Figure 3A:
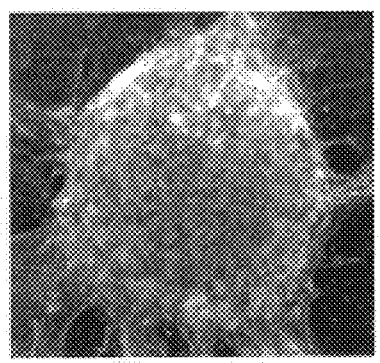
FIGS. 3A–3D are a series of photographs showing clusters of MAP2-positive/TH-positive cells that are spherical and tightly-packed (FIGS. 3A and 3C) and those that are ovoid and much less densely-packed (FIGS. 3B and 3D).
Figure 3B:
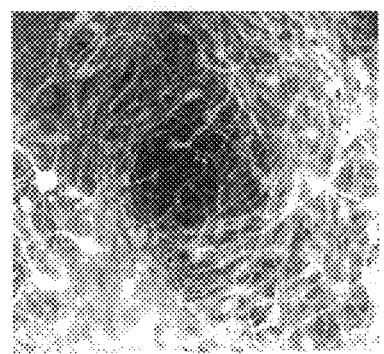
Figure 3C:
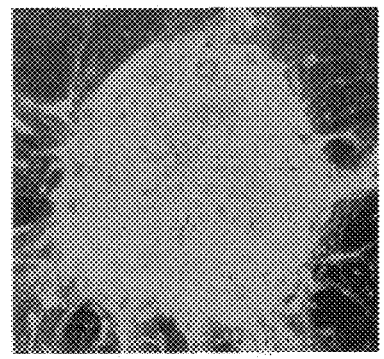
Figure 3D:
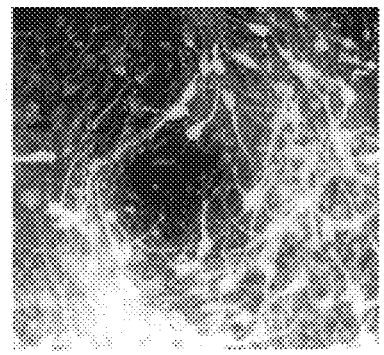

As illustrated in FIG. 2, the MAP2-positive/TH-positive cells exhibited a variety of mature morphologies typical of post-mitotic dopaminergic neurons in vitro (Shimoda et al., Brain Res. 58 6:319–331; 1992), and in vivo (Tepper et al., Neuroscience 60:469–477; 1994). In all cases of successful expansion, the MAP2-positive/TH-positive cells occurred in clusters that varied in shape from tightly-packed spheres (FIGS. 3A and 3C), to less densely packed ganglion-like structures (FIGS. 3B and 3D).

EXAMPLE 2

Re-aggregate Size and Viability

Figure 4A:
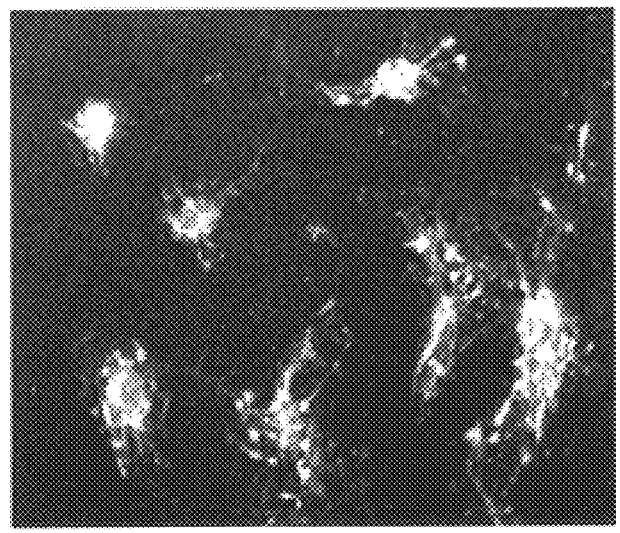
FIGS. 4A and 4B are a series of photomicrographs of cell aggregates of 50 to 200 cells.
Figure 4B:

Some of the expanded clusters were detached by exposure to papain (10 U/mL, 5 min, 37° C.), and, after washing, were dispersed at a density of $1.0 \times 10_6$ cells/mL in 1.5 mL Eppendorf tubes and placed on a rotary shaker at eight revolutions/min, at room temperature, for four hours. Under these conditions, aggregates of 50–200 cells were formed. Some of the aggregates were plated in plastic 8-well chamber slides, and incubated for twelve hours. They were then stained to visualize TH, as illustrated in FIG. 4. An estimated 25–50% of the cells in these aggregates were TH-positive (FIG. 4). Some of the aggregates were incubated in $Mg^{2+}$-free Dulbecco's phosphate-buffered saline (DPBS), containing 0, 1.0 or 2.5 mM $Ca^{2+}$, at 4° C., for up to six hours. At intervals, we dispersed some of the aggregates and determined cell viability. We found that, provided the cells are kept on ice and at a calcium concentration of 1.0 mM or less, the cells in the aggregates of 50 to 200 cells remain at 90–98% viability for at least six hours. Increasing the $Ca^{2+}$ concentration to 2.5 mM, however, caused a rapid decrease in viability (10–40%).

Figure 5:
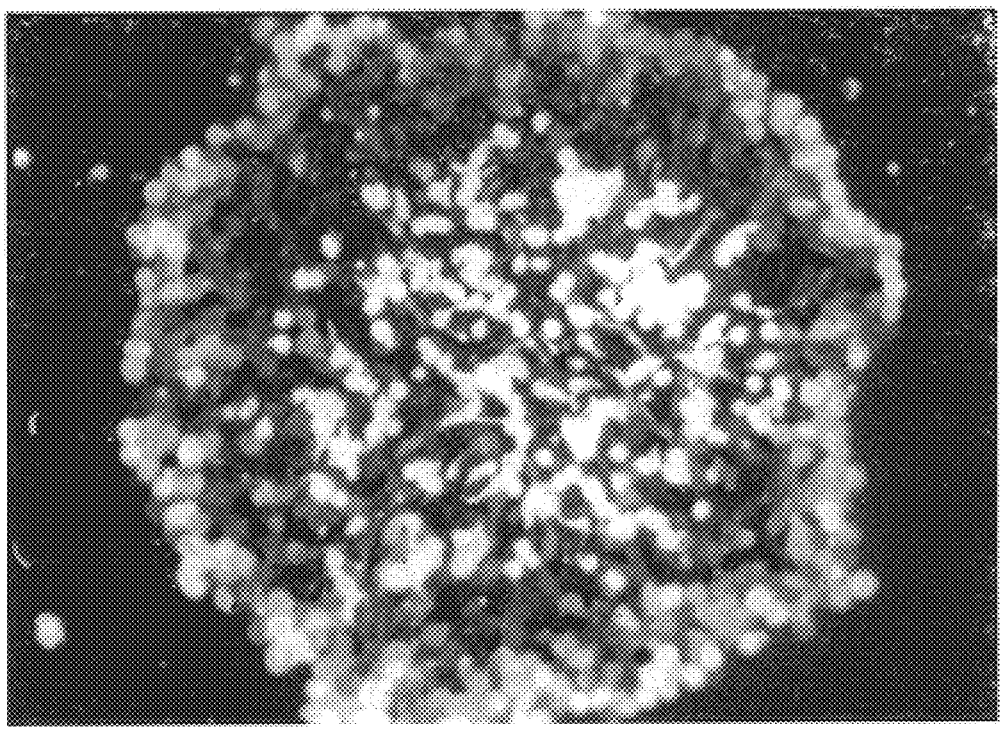
FIG. 5 is a photograph showing that, in aggregates of>1,000 cells, the cells at the center of the large aggregate were non-viable, while the cells at the periphery remained viable for several hours.

In order to test cell viability in the aggregates as a function of size, aggregates of >1,000 cells were prepared by increasing the density of the dispersed cells to $2.5 \times 10^6$/ml. We found that in all of the large rosette-like aggregates produced under these experimental conditions, the cells at the center of the cluster died rapidly, while the cells at the periphery remained viable (FIG. 5). Cell death in these large aggregates occurred under the same conditions that supported 90–98% cell viability in the smaller aggregates of 50–200 cells. These results indicate that when minced mesencephalic tissue is used for transplantation, the viability of the cells at the center of the minced pieces of tissue are likely to be dead even before transplantation.

The methods being used successfully to manipulate human, mesencephalic dopaminergic neurons in culture were modeled directly on those used for rat dopaminergic neurons (Meyer et al., Exp. Brain Res. 119:345–355, 1998; Dong et al., Neurosci. Lett. 178:27–31, 1994). There is therefore a reasonable presumption that the protocols reported herein for the expansion of rat neural progenitor cells will be applicable to human neural progenitor cells. An appropriate developmental age is likely to be approximately 6.5–7.5 weeks of gestation, although earlier and later ages are also likely to be suitable sources of neural progenitor cells (Silani et al. Exp. Neurol. 128:59–76, 1994; Freeman et al., Exp.Neurol. 113:344–353, 1991).

Successful expansion occurred only when the cells were plated as MIs, in which <5% of the surface area of the culture dish was covered with cells, and never when the entire culture dish was plated. Cell density is not a likely issue, since the density was greater in the MI cultures ($5.0 \times 10_4$ cells/cm$^2$) versus the conventional cultures ($3.5 \times 10_4$ cells/cm$^2$). The most important variable may therefore be the medium volume in relation to the number of cells plated. This is supported by our observations of cell number in trials that resulted in failure ($1.0 \times 10_6$ cells) versus success ($5.0 \times 10_4$ cells). In both the successful and unsuccessful trials, about 75% of the cells died during the first three days of culture. One possibility is that the concentration of a toxin released by dead cells was high enough in the conventional cultures to kill the neural progenitor cells.

EXAMPLE 3

Transformation of Cell Aggregates

In therapy for neurodegenerative diseases, it may be desirable to transplant cells that are genetically modified to survive the insults that caused the original neurons to die. In addition, cell aggregates may be used to deliver therapeutic proteins into the brain of patients with neurodegenerative disorders to prevent death of host cells. In still another example, undifferentiated cells in the cell aggregates can be induced to differentiate into a desired cell type by transforming the cells with nucleic acid molecules encoding proteins that regulate cell fate decisions (e.g., transcription factors such as isl-1, en-1, en-2 and nurr-1, implicated in regulating motomeuron and striatal phenotypes). Using such a method, it is possible to induce the differentiation of the specific cell types required for transplant therapy. Therefore, it would be advantageous to transform cells within cell aggregates (either prior or subsequent to aggregation) with nucleic acid molecules encoding desired proteins.

EXAMPLE 4

Transplantion of Cell Aggregates Into Adult Rodent Brain

One therapeutic use for the cell aggregates of the present invention is autologous transplantation into the injured or degenerating CNS or PNS, to replace lost cell types and/or to express therapeutic molecules. These methods can be validated using a rodent model for Parkinson's disease. In this model, dopaminergic innervation of the adult striatum is destroyed by a local infusion of 6-hydroxydopamine under conditions in which noradrenergic neurons are spared. Several weeks later, cell aggregates are then transplanted into both the intact and lesioned striatum. One week later, the fate of the transplanted cells is determined by standard methods (e.g., immunohistochemistry).

In one example, the dopaminergic innervation to adult rat striatum is first unilaterally lesioned with the neurotoxin 6-hydroxydopamine. The efficacy of the lesions is tested two weeks later by amphetamine-induced rotational behavior. Two days prior to transplantation, rats are irnmunosuppressed with cyclosporin. Cell aggregates, produced as described herein, are then stereotactically injected into the caudate-putamen complex on both the lesioned and unlesioned sides. Sixteen days following transplantation, animals are sacrificed, and sections of the striatum are analyzed for presence of the transplanted cells.

To confirm that identified cells are derived from the cell aggregates,experiments in which the transplanted cells are detectably-labeled can be performed. In one set of experiments, transplanted cells are derived from transgenic mice in which a neuron-specific promoter drives expression of a β-galactosidase marker gene. Immunohistochemical analysis of animals receiving the transgenic cells should reveal the presence of β-galactosidase-positive neurons within the transplant tract, confirming that the transplanted cells survived. In a second set of experiments, cells are labeled with BrdU for 18 hours, washed to remove the BrdU label, and then transplanted unilaterally into the 6-hydroxydopamine-lesioned striatum of animals prepared as described herein. Immunohistochemical analysis with anti-BrdU should reveal that all animals showed evidence of BrdU-positive cells.

The foregoing results are obtained using the following materials and methods.

Dissection of Tissue, Cell Dispersal and Microisland Cultures

Timed-pregnant, E9, Sprague Dawley rats were obtained from Taconic Farms, and housed for three days. At E12, the rats were killed by exposure to $CO_2$. The abdominal region of the rat was swabbed with 70% EtOH, a laparotomy was done, and the uterine sac removed and stored in cold Hank's balanced salt solution (HBSS), at pH 7.4. The ventral mesencephalon (VM), with the floor plate intact, was localized, micro-dissected in a 10 cm petri dish in fresh, cold HBSS, thoroughly cleared of non-neural tissue, and stored in 5 mL of HBSS in a 15 mL, conical tube, on ice. After tissue collection, the HBSS was aspirated, and the tissue rinsed with two changes of N2 medium (consisting of a 1:1 mixture if F12 and DMEM containing 25 $\mu$g/mL insulin, 100 $\mu$g/mL apotransferrin, 100 $\mu$M putrescine, 20 nM progesterone, and 1.55 mg/mL glucose), then dispersed in 2 mL of N2 medium, which was used in all subsequent procedures. The tissue was then triturated to disperse the cells completely. The cells were centrifuged for 2 minutes at 1,000 rpm (470×g), the medium aspirated, and the pellet dispersed in N2 medium. The cells were counted using a hemocytometer, and the density adjusted to $2.5 \times 10_5$ cells/mL. It is important to avoid even traces of cell debris in the cultures. MI droplets of 25 $\mu$L (6,250 cells), covering an area of 12.5 $m_2$, equivalent to $5.0 \times 10_4$ cells/cm$^2$, were plated in dry 6 cm, plastic petri dishes, coated with polyomithine (15 $\mu$g/mL) and fibronectin (1.0 $\mu$g/mL), in a 3×3 array. The dishes were transferred to the incubator (37° C., 5% $CO_2$, 100% humidity) for 15 min. Following cell attachment, 2.25 mL of N2 growth medium was gently added to each dish plus bFGF (10 ng/mL) (Upstate Biotechnologies, Lake Placid, N.Y.). The cultures were treated daily with bFGF, and the growth medium changed daily for the first three days, then every second day. An estimated 75% of the cells died by DIV3. Cell expansion was not evident until DIV3, then progressed rapidly. At DIV9, bFGF was withdrawn, and cell maturation allowed to continue until DIV12.

Formation of Cell Aggregates

At DIV9, the expanded cells were treated with papain (10 U/ml) for 10 min, at 37° C., then washed in 5 mL N2 medium containing 2.5% of fetal bovine serum (FBS). After centrifugation, the pellet was resuspended in N2 medium, and the density adjusted to $1.0 \times 10_6$ or $2.5 \times 10_6$ cells/mL. Cell viability was tested using the Live Cell Dead Cell kit (L-3224; Molecular Probes, Eugene, OR), as described previously (Takeshima et al., J. Neurosci. 14:4769–4779, 1994), and found to be >95%. The cell suspension was transferred to 1.5 Eppendorf tubes (1.4 mL/tube), and rotated at eight revolutions per minute, for 4 hr, at room temperature. The tube was then centrifuged (52×g, 3 min), the medium aspirated, new medium added to produce a density equivalent to $2.0 \times 10_6$ cell/mL, and the pellet very gently dispersed by tapping. The cells were plated in 50 $\mu$L MI droplets, and incubated. The cultures were stained for TH at 12 h after plating. The results demonstrate that during the rotation procedure, in cell suspensions of $1.0 \times 10_6$ cells/niL, small aggregates of 50–200 cells were formed, and that about 30–50% of the cells were TH-positive (FIG. 4). In the tubes that contained cells at a density of $2.5 \times 10_6$ cells/mL, much larger aggregates were formed (~1000 cells/aggregate). Moreover, viability testing demonstrated that the cells at the center of the larger aggregates died rapidly, while the cells at the periphery remained viable.

Viability of Cells in Small Aggregates

At the end of the 4 hr aggregation period, some tubes were centrifuged (500 rpm, 3 min), and the medium aspirated and replaced by 0.5 mL Dulbecco's phosphate-buffered saline (DPBS) (0 mM $Ca^{2+}$, 0 mM $Mg^{2+}$). The aggregates were suspended by gentle tapping. The tubes were placed on ice, and agitated gently. At intervals, some of the 50–200 cell aggregates were redispersed by trituration only, and cell viability tested, and found to be 90–98% throughout. When calcium was increased to 2.5 mM, however, there was a rapid decline in viability (<40% viable) starting at 1 hour.

Sources of Immunochemicals and Neurotrophic Factors

Mouse monoclonal anti-MAP2 (Cat. No. 1284959) and anti-mouse IgG-FITC (Cat. No. 1814222) and anti-rabbit IgG-rhodamine (Catalog No. 0605170) antibodies were obtained from Boehringer-Mannheim (Indianapolis, MN). Rabbit polyclonal anti-TH antibody was obtained from the Incstar Corporation (Stillwater, MN). The live cell dead cell kit was obtained from Molecular Probes (Eugene, OR). Fetal calf serum (FCS) was purchased from Gibco (#16000-044).

The foregoing transplantation experiments are performed using the following methods. Rats or mice weighing 180–200 g or 25–30 g, respectively, were anaesthetized with a mixture of ketamine (90 mg/kg) and xylazine (10 mg/kg) (intraperitoneal) prior to stereotactic injections of 24 $\mu$g of 6-hydroxydopamine hydrobromide (dissolved in 5 $\mu$L of 0.9% saline containing 0.2 mg/ml ascorbate) into the right medial forebrain bundle (Tooth bar:-2.4 mm; A:-4.4 mm; L: 1.0 mm; V:7.5 mm). Two weeks after the lesion, animals are tested for rotational behavior. Animals are immunosuppressed with cyclosporine (40 mg/kg, intraperitoneal) once a day until the day of sacrifice. For cell aggregate transplantation, anaesthetized animals are mounted in a stereotactic apparatus, and 2×2.5 $\mu$L aliquots of cell aggregates are injected unilaterally (into the lesioned caudate putamen) or bilaterally. The injections are made using, for example, a 5 $\mu$L Hamilton syringe at the following coordinates: Tooth bar, -2.4 mm; A: 0.2; L: 3.0; V: 5.5–6.0. Injections are performed over a period of three minutes, a further five minutes is allowed for diffusion, and the needle is then retracted smoothly and slowly. These 5 $\mu$L injections contain between 500 and 1000 cell aggregates. For the BrdU experiments, BrdU (10 $\mu$M) is added to culture media for 18 hours, after which the cells are washed three times with fresh media to remove the BrdU, and then transplanted one day later. Approximately two weeks following transplantation, animals are anaesthetized with an overdose of i.p. pentobarbital and perfused transcardially sequentially with saline and 4% formaldehyde in phosphate buffer (PB, 0.1M, pH 7.4). The brains are post-fixed for 18 hours at 4° C., and then cryoprotected for 48 hours in 30% sucrose dissolved in PB. Brains are sectioned on a freezing microtome in the coronal plane at 40 $\mu$m. Free-floating sections are collected in phosphate buffered saline (0.1M, PBS) and processed for immunohistochemistry. Sections are initially incubated in a PBS solution containing 0.5% sodium borohydride for 20 minutes, rapidly washed six times, and then incubated in PBS containing 5% BSA. Sections are then incubated in a PBS solution containing 0.1% Triton X-100, 2% BSA and an appripriate primary antibody. After overnight incubation in the primary antibodies at 4° C., sections are at room temperature in PBS containing biotinylated goat anti-rabbit IgG, 0.1% Triton X-100, and 2% BSA. After three brief washes in PBS, sections are incubated for one hour at room temperature in PBS containing an avidin-biotin complex. Following three washes in PBS, the immunohistochemical reaction product is revealed by incubation in Tris buffer (0.05M, pH 7.6) containing diaminobenzidine tetrahydrochloride (DAB) (0.025 g/100 mL), 1% 1M imidazole, and 0.3% hydrogen peroxide. Sections are exposed to DAB for 15 minutes, rinsed six times in PBS, mounted onto chrom-alum coated slides, air dried, dehydrated in graded alcohols, and coverslipped.

OTHERS EMBODIMENTS

The present invention has been described in terms of particular embodiments found or proposed by the present inventors to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

All publications, patents and patent applications are herein incorporated by reference in their entirety to the same extent as if each individual publication, patent or patent application was specifically and individually indicated to be incorporated by reference in its entirety.

What is claimed is:

1. A method for producing aggregates of neuronal cell preparation, said method comprising:

(a) providing a cell culture comprising neural progenitor cells;

(b) culturing said cells in a serum-free medium containing a mitogen, wherein said medium is sufficient for expansion of the cells;

(c) dissociating said expanded cells to provide a cell suspension comprising single cells, aggregates of fewer than two hundred cells, or a combination thereof; and (d) aggregating said expanded cells in said cell suspension, wherein said aggregation results in greater than 90% of cell aggregates consisting of between 50 and 200 meuronal cells/aggregate, and wherein said cells in said cell aggregates are suitable for transplantation.

2. The method of claim 1, wherein said cells comprise tyrosine hydroxylase-positive cells.

3. The method of claim 2, wherein said tyrosine hydroxylase-positive cells produce dopamine.

4. The cell aggregate of claim 1, wherein greater than 20% of said cells are tyrosine hydroxylase positive.

5. The method of claim 1, wherein said cells are human cells.

6. A neuronal cell aggregate preparation, wherein greater than 90% of said cell aggregates in said preparation are between 50 and 200 cells, and wherein greater than 20% of said cells in said aggregates are tyrosine hydroxylase-positive.

7. The cell aggregate of claim 6, wherein said aggregate consist of between 50 and 200 cells.

8. The cell aggregate of claim 6, wherein greater than 30% of said cells are tyrosine hydroxylase-positive.

9. The cell aggregate of claim 8, wherein said tyrosine-hydroxylase cells produce dopamine.

10. The cell aggregate of claim 6, wherein said cells are human cells.

* * * * *